(12) United States Patent
Wibaux et al.

(10) Patent No.: US 11,058,793 B2
(45) Date of Patent: Jul. 13, 2021

(54) ADHESIVE CONTAINING MICROPARTICLES

(75) Inventors: Anne Marie Wibaux, Cleveland Heights, OH (US); Peter Johnson, Raleigh, NC (US)

(73) Assignee: Avery Dennison Corporation, Glendale, CA (US)

( * ) Notice: Subject to any disclaimer, the term of this patent is extended or adjusted under 35 U.S.C. 154(b) by 2046 days.

(21) Appl. No.: 14/117,381

(22) PCT Filed: May 11, 2012

(86) PCT No.: PCT/US2012/037429
§ 371 (c)(1),
(2), (4) Date: Nov. 13, 2013

(87) PCT Pub. No.: WO2012/158483
PCT Pub. Date: Nov. 22, 2012

(65) Prior Publication Data
US 2015/0056291 A1   Feb. 26, 2015

Related U.S. Application Data

(60) Provisional application No. 61/486,379, filed on May 16, 2011.

(51) Int. Cl.
| | | |
|---|---|---|
| A61L 24/00 | (2006.01) | |
| A61L 26/00 | (2006.01) | |
| C09J 11/00 | (2006.01) | |
| C08L 75/04 | (2006.01) | |
| C08K 7/16 | (2006.01) | |

(52) U.S. Cl.
CPC ....... *A61L 24/0015* (2013.01); *A61L 24/0047* (2013.01); *A61L 26/0066* (2013.01); *C09J 11/00* (2013.01); *C08K 7/16* (2013.01); *C08L 75/04* (2013.01)

(58) Field of Classification Search
None
See application file for complete search history.

(56) References Cited

U.S. PATENT DOCUMENTS

| | | |
|---|---|---|
| 2,736,721 A | 2/1956 | Dexter |
| 4,199,567 A | 4/1980 | Rankin |
| 4,310,509 A | 1/1982 | Berglund et al. |
| 4,434,181 A | 2/1984 | Marks, Sr. et al. |
| 4,460,369 A | 7/1984 | Seymour |
| 4,600,001 A | 7/1986 | Gilman |
| 4,753,232 A | 6/1988 | Ward |
| 4,941,882 A | 7/1990 | Ward et al. |
| 4,990,144 A | 2/1991 | Blott |
| 5,018,516 A | 5/1991 | Gilman |
| 5,069,907 A | 12/1991 | Mixon et al. |
| 5,214,119 A | 5/1993 | Leir et al. |
| 5,270,358 A | 12/1993 | Asmus |
| 5,322,695 A | 6/1994 | Shah et al. |
| 5,340,581 A | 8/1994 | Tseng et al. |
| 5,382,451 A | 1/1995 | Johnson et al. |
| 5,389,376 A | 2/1995 | Duan et al. |
| 5,441,741 A | 8/1995 | Cheong |
| 5,614,310 A | 3/1997 | Delgado et al. |
| 5,686,096 A | 11/1997 | Khan et al. |
| 5,702,721 A | 12/1997 | Horstmann et al. |
| 5,717,005 A | 2/1998 | Richardson |
| 5,763,412 A | 6/1998 | Khan et al. |
| 5,908,693 A * | 6/1999 | Delgado ............... A61F 13/023 428/343 |
| 6,043,406 A | 3/2000 | Sessions et al. |
| 6,228,354 B1 | 5/2001 | Jeng |
| 6,455,086 B1 | 9/2002 | Trinh et al. |
| 6,458,341 B1 | 10/2002 | Rozzi et al. |
| 6,495,158 B1 | 12/2002 | Buseman et al. |
| 6,518,359 B1 | 2/2003 | Clemens et al. |
| 6,565,873 B1 | 5/2003 | Shefer et al. |
| 6,589,562 B1 | 7/2003 | Shefer et al. |
| 6,599,525 B2 | 7/2003 | Scamilla Aledo et al. |
| 6,642,304 B1 | 11/2003 | Hansen et al. |
| 6,733,745 B2 | 5/2004 | Rozzi et al. |
| 6,742,522 B1 | 6/2004 | Baker |
| 6,844,306 B2 | 1/2005 | Werle et al. |
| 6,893,655 B2 | 5/2005 | Flanigan et al. |
| 7,160,976 B2 | 1/2007 | Luhmann et al. |
| 7,674,473 B2 | 3/2010 | Falder et al. |

(Continued)

FOREIGN PATENT DOCUMENTS

| | | |
|---|---|---|
| AU | 1985043241 | 12/1985 |
| CA | 1207228 | 7/1986 |

(Continued)

OTHER PUBLICATIONS

Internationai Search Report and Written Opinion issued in corresponding IA No. PCT/US2012/037429 dated Jan. 21, 2013.

(Continued)

*Primary Examiner* — Dominic Lazaro

(57) ABSTRACT

Methods for forming and incorporating microparticles containing one or more active agents into adhesives are described. The methods involve spray drying a liquid of the one or more active agents and obtaining the active agent in a particulate form. The dry powder is then blended or otherwise incorporated with the adhesive of interest. Also described are various medical products utilizing the adhesive and one or more active agents in microparticle form, and related methods of use.

13 Claims, No Drawings

(56) References Cited

U.S. PATENT DOCUMENTS

| | | | |
|---|---|---|---|
| 7,683,216 B2 | 3/2010 | Dubois et al. | |
| 7,704,523 B2 | 4/2010 | Serafica et al. | |
| 7,824,122 B2 | 11/2010 | Flores et al. | |
| 8,623,935 B2 | 1/2014 | Hobbs et al. | |
| 8,969,649 B2 | 3/2015 | Leibowitz et al. | |
| 9,101,134 B2 | 8/2015 | Huang et al. | |
| 9,278,155 B2 | 3/2016 | Asmus et al. | |
| 9,346,981 B2 | 5/2016 | Wibaux et al. | |
| 9,592,161 B2 | 3/2017 | Rule et al. | |
| 9,764,059 B2 | 9/2017 | Wibaux et al. | |
| 9,801,902 B2 | 10/2017 | Smith et al. | |
| 10,329,384 B2 | 6/2019 | Hansen et al. | |
| 10,456,498 B2 | 10/2019 | Wibaux | |
| 2002/0018814 A1 | 2/2002 | Werle et al. | |
| 2002/0072480 A1 | 6/2002 | Werle et al. | |
| 2003/0077316 A1 | 4/2003 | Nichols et al. | |
| 2003/0212005 A1 | 11/2003 | Petito | |
| 2004/0009202 A1 | 1/2004 | Woller | |
| 2004/0063792 A1 | 4/2004 | Khera et al. | |
| 2004/0109869 A1 | 6/2004 | Glenn et al. | |
| 2004/0170794 A1 | 9/2004 | Verhaert | |
| 2004/0241214 A1* | 12/2004 | Kirkwood | A61F 13/0213 424/445 |
| 2005/0049365 A1 | 3/2005 | Cleary et al. | |
| 2005/0118246 A1 | 6/2005 | Wong et al. | |
| 2005/0244346 A1 | 11/2005 | Nakao et al. | |
| 2005/0249791 A1 | 11/2005 | Hobbs et al. | |
| 2007/0116729 A1 | 5/2007 | Paiepu | |
| 2007/0259029 A1 | 11/2007 | McEntire et al. | |
| 2008/0220045 A1 | 9/2008 | Shalaby et al. | |
| 2008/0233177 A1 | 9/2008 | Meconi | |
| 2009/0130157 A1 | 5/2009 | Ylitalo et al. | |
| 2010/0022654 A1 | 1/2010 | Asmus et al. | |
| 2010/0029779 A1 | 2/2010 | Street et al. | |
| 2010/0081672 A1 | 4/2010 | Wan et al. | |
| 2010/0303878 A1 | 12/2010 | Slager et al. | |
| 2010/0322996 A1 | 12/2010 | Wibaux et al. | |
| 2011/0067799 A1 | 3/2011 | Mussig et al. | |
| 2012/0078155 A1 | 3/2012 | Bowman et al. | |
| 2012/0245538 A1 | 9/2012 | Horstmann et al. | |
| 2012/0328682 A1 | 12/2012 | Bardwell et al. | |
| 2013/0072566 A1 | 3/2013 | Asmus et al. | |
| 2013/0239977 A1 | 9/2013 | McGuire, Jr. | |
| 2013/0243841 A1 | 9/2013 | Kommareddy et al. | |
| 2013/0303656 A1 | 11/2013 | Wibaux et al. | |
| 2014/0322299 A1 | 10/2014 | Wibaux | |
| 2015/0056291 A1 | 2/2015 | Wibaux et al. | |
| 2015/0367021 A1 | 12/2015 | Wibaux | |
| 2016/0000609 A1 | 1/2016 | Van Holten et al. | |
| 2016/0030248 A1 | 2/2016 | Potters | |
| 2016/0228600 A1 | 8/2016 | Wibaux et al. | |
| 2017/0007464 A1 | 1/2017 | Liu et al. | |
| 2017/0095431 A1 | 4/2017 | Andrews et al. | |
| 2020/0016291 A1 | 1/2020 | Wibaux | |

FOREIGN PATENT DOCUMENTS

| | | |
|---|---|---|
| CA | 2333009 | 12/1999 |
| CN | 1522687 | 8/2004 |
| CN | 1961666 | 5/2007 |
| CN | 101653431 | 2/2010 |
| EP | 0066899 | 12/1982 |
| EP | 0404558 | 12/1990 |
| EP | 0328421 | 4/1993 |
| EP | 0361722 | 12/1993 |
| EP | 1139981 | 4/2002 |
| EP | 1203531 | 11/2003 |
| EP | 1784232 | 5/2007 |
| EP | 3280769 | 2/2018 |
| EP | 3368086 | 9/2018 |
| EP | 2968014 | 4/2019 |
| GB | 2274586 | 8/1994 |
| JP | 1990-147063 | 6/1990 |
| JP | 1994508287 | 9/1994 |
| JP | 6-509955 | 11/1994 |
| JP | 2825549 | 11/1998 |
| JP | 2002179513 | 6/2002 |
| JP | 2002-272831 | 9/2002 |
| JP | 2002-332228 | 11/2002 |
| JP | 2003534310 | 11/2003 |
| JP | 2004010545 | 1/2004 |
| JP | 2007502319 | 2/2007 |
| JP | 2007-526348 | 9/2007 |
| JP | 2007-536261 | 12/2007 |
| JP | 2014510038 | 4/2014 |
| WO | 90/13780 | 11/1990 |
| WO | 1993/00118 | 1/1993 |
| WO | WO9300118 | 1/1993 |
| WO | 1993002717 | 2/1993 |
| WO | WO199302717 | 2/1993 |
| WO | 1993/03649 | 3/1993 |
| WO | WO9303649 | 3/1993 |
| WO | WO1999000025 | 1/1999 |
| WO | 1999023150 | 5/1999 |
| WO | WO992470 | 12/1999 |
| WO | WO2000/036353 | 6/2000 |
| WO | 2000/061692 | 10/2000 |
| WO | WO2000/061692 | 10/2000 |
| WO | 2003/103618 | 12/2003 |
| WO | 2004/080499 | 9/2004 |
| WO | 2009/064291 | 5/2009 |
| WO | WO2010080936 | 7/2010 |
| WO | 2011/009083 | 1/2011 |
| WO | WO2011088072 | 7/2011 |
| WO | WO2012100244 | 7/2012 |
| WO | WO2013074628 | 5/2013 |
| WO | 2013/090191 | 6/2013 |
| WO | 2014/124232 | 8/2014 |
| WO | 2014/151355 | 9/2014 |
| WO | 2015/188031 | 12/2015 |
| WO | 2015187632 | 12/2015 |

OTHER PUBLICATIONS

Giunchedi, et al. "Formulation and in vivo evaluation of chlorhexidine buccal tablets prepared using drug-loaded chitosan microspheres," European Journal of Pharmaceutics and Biopharmaceutics, Elsevier Science Publishers B.V., Amsterdam, NL, vol. 53, No. 2, Mar. 1, 2002, pp. 233-239, XP004342819, ISSN: 0939-6411, DOI: 10.1016/S0939-6411(01)00237-5 Section 2.2 Preparation by spray-drying; table 2.

International Search Report and Written Opinion issued in corresponding IA No. PCT/US2012/022162 dated Aug. 10, 2012.

Avery Dennison Medical Solutions Demonstrates the Efficacy of its new Chlorhexidine Gluconate Adhesive Delivery System, Avery Dennison Medical Solutions, Sep. 13, 2011, 1-2.

Boddupalli, et al., Mucoadhesive drug delivery system: An overview, Jounal of Advanced Pharmaceutical Technology & Research, vol. 1, 2010, 381-387.

Ceballos, et al., Influence of formulation and process variables on in vitro release of theophylline from directly-compressed Eudragit matrix tablets, II Farmaco, Jan. 15, 2005, 913-918, vol. 60, No. 11-12.

Cui, et al., Bilayer Films for Mucosal (Genetic) Immunization via the Buccal Route in Rabbits, Pharmaceutical Research, Jul. 2002, 947-953, vol. 19, No. 7.

Eudragit, acrylic polymers for solid oral dosage forms, Jan. 1, 2008, 1-11.

International Search Report and Written Opinion issued in corresponding IA No. PCT/US2014/025549 dated Jul. 25, 2014.

International Search Report and Written Opinion of the International Searching Authority, or the Declaration issued in corresponding IA No. PCMS14/15263 dated Sep. 19, 2014.

International Search Report and Written Opinion of the International Searching Authority, or the Declaration issued in corresponding IA No. PCT/US2015/033689 dated Sep. 8, 2015.

International Search Report and Written Opinion of the International Searching Authority, or the Declaration issued in corresponding IA No. PCT/US2012/065014 dated Feb. 15, 2013.

(56) References Cited

OTHER PUBLICATIONS

Invitation to Pay Additional Fees issued in corresponding IA No. PCT/US2012/022162.
Maruzen, "New Experimental Chemistry Course 1 Basic Operation I", Sep. 20, 1975, 459-463.
Yue, et al., A novel polymeric chlorhexidine delivery device for the treatment of periodontal disease, Biomaterials, vol. 25, 2004, pp. 3743-3750.
International Search Report and Written Opinion of the International Searching Authority, or the Declaration issued in corresponding IA No. PCT/US2015/034336 dated Mar. 23, 2016.
International Preliminary Report on Patentability dated Nov. 19, 2013 issued in corresponding IA No. PCT/US2012/037429 filed May 11, 2012.
Pei, et al. "Plant Fiber Chemistry", pp. 244-246, China Light Industry Press, Jul. 2012.
International Preliminary Report on Patentability dated May 20, 2014 issued in corresponding IA No. PCT/US2012/065014 filed Nov. 14, 2012.
Sateesh Kandavilli: "Polymers in Transdermal Drug Delivery Systems," Pharmaceutical Technology, May 31, 2002, XP055101101, Retrieved from the internet:. http://www.pharamtech.com/pharmtech/data/articlestandard/pharmtech/192002/18600/article.pdf [retrieved on Feb. 10, 2014].
Luo, et al., A Complete Collection of Pharmaceutical Excipients, Sichuan university of science and technology press, Jan. 31, 2006, 53-56.
International Preliminary Report on Patentability dated Dec. 6, 2016 issued in corresponding IA No. PCT/US2015/034336 filed Jun. 5, 2015.
He et al., General Practitioner's Guidelines for Medication Use, Beijing Science and Technology Press, Nov. 30, 2010, 1205.
Yao, Application Directory of Pharmaceutical Excipients, China Medical Science and Technology Press, Aug. 31, 2011, 1342-1347.
International Preliminary Report on Patentability dated Jul. 6, 2015 issued in corresponding IA No. PCT/US2014/015263 filed Feb. 7, 2014.
Invitation to Pay Additional Fees dated May 22, 2014 issued in corresponding IA No. PCT/US2014/015263 filed Feb. 7, 2014.
International Preliminary Report on Patentability dated Sep. 24, 2015 issued in corresponding IA No. PCT/US2014/025549 filed Mar. 13, 2014.
International Preliminary Report on Patentability dated Jul. 23, 2013 issued in corresponding IA No. PCT/US2012/022162 filed Jan. 23, 2012.
International Preliminary Report Patentability dated Dec. 6, 2016 issued in corresponding IA No. PCT/US2015/033689 filed Jun. 2, 2015.

* cited by examiner

ADHESIVE CONTAINING MICROPARTICLES

CROSS REFERENCES TO RELATED APPLICATIONS

The present application is a 371 of International Application No. PCT/US2012/037429, which was published in English on Nov. 22, 2012, which claims priority to U.S. Provisional Patent Application No. 61/486,379 filed May 16, 2011, which is incorporated herein by reference in its entirety.

FIELD

The present invention relates to adhesives containing microparticles of one or more active agents, methods for incorporating microparticles of actives into an adhesive, and products using such adhesives.

BACKGROUND

A wide array of medical products use adhesive for affixing the product onto a user's skin. As will be appreciated, it is desirable to include one or more active agents such as antimicrobial agents in the medical product or adhesive to prevent or at least minimize microbial growth or reproduction along the skin, as such can readily lead to infection and other undesirable conditions.

Accordingly, artisans have attempted to incorporate a wide range of antimicrobial agents into medical products or materials. Although certain agents have been incorporated into adhesives, effective incorporation into an adhesive composition presents a formidable technical challenge. It is difficult to efficiently disperse such agents within the adhesive. Furthermore, certain antimicrobial agents undergo a loss in efficacy upon incorporation in an adhesive formulation due to the presence of solvents or other components in the adhesive.

Accordingly, it would be desirable to provide a method for incorporating one or more active agents and particularly an antimicrobial agent into an adhesive formulation such that the agent is effectively dispersed and retains its efficacy when residing in the adhesive.

SUMMARY

The difficulties and drawbacks associated with previously known compositions, products, and practices are addressed in the present methods, adhesive compositions, products using such compositions and related methods of use.

In one aspect, the present subject matter provides an adhesive composition comprising an adhesive and microparticles dispersed in the adhesive. The microparticles include a matrix material and at least one active agent.

As will be realized, the subject matter is capable of other and different embodiments and its several details are capable of modifications in various respects, all without departing from the invention. Accordingly, the description is to be regarded as illustrative and not restrictive.

DETAILED DESCRIPTION OF THE EMBODIMENTS

The present subject matter generally provides an adhesive composition comprising microparticles that include one or more active agents. The present subject matter also provides various methods relating to the preparation of the adhesives and microparticles, and various products using such adhesives.

Active Agents and Forming Microparticles

A wide array of one or more active agents can be incorporated in the adhesives described herein. Preferably, the active agents are hydrophilic. Non-limiting examples of preferred active agents include benzocaine, procaine hydrochloride, tetracaine, tetracaine hydrochloride, dibucaine, lidocaine, lidocaine hydrochloride, bupivicaine, dyclonin, etidocaine, mepivicaine, butamen picrate, dimethisoquin hydrochloride, cyclomethylcaine sulfate, and the like; analgesics and anti-inflammatory agents such as buprenorphin, butophanol tartrate, acetaminophen, fentanyl, mefenamic acid, flutenamic acid, diclofenac, oxyphenbutazone, phenybutazone, ibuprofen, flurbiprofen, naproxen, menthol, methyl salicylate, phenol, salicylic acid, benzyl alcohol, camphor, camphorated metacresol, juniper tar, resorcinol, allyl isothiocyanate, capsaicin, and the like; corticosteroids such as alclometasone dipropionate, amcinocide, hydrocortisone, betamethasone dipropionate, betamethasone valerate, desoximetasone, clobetasol propionate, flurandrenolide, halcinonide, halobetasol, estradiol, testosterone, progesterone, fluticasone, clobetasol, dexamethasone, dexonide, fluocinolone acetonide, flucinonide, medroxyprogesterone, mometasone furoate, triamcinolone, and the like; antibiotics such as bacitracin, bacitracin zinc, chlortetracycline hydrochloride, chlorhexadine gluconate, clindamycin, cliquinol, neomycin sulfate, polymyxin B sulfate, erythromycin, gentamicin, sulfathiazole, sulfacetamide, sulfabenzamide, oxytetracycline hydrochloride, tetracycline, and the like; antimicrobial agents such as benzalkonium chloride, chlorhexidine gluconate, hexachlorophene, mafenide acetate, nitrofurazone, nystatin, acetosulfamine, clortrimazole, povidone-iodine, and the like; antifungal agents such as amphotericin B, butoconazole, cetylpyridinium chloride, chlorxylenol, cyclopirox olamine, clioquinol, clotrimazole, sulconazole nitrate, nystatin, oxyconazole, econazole nitrate, ketoconazole, miconazole nitrate, naftifine hydrochloride, pentamycin, pyrrolinitrin, terbinafine, triacetin, and the like; debriding agents such as deoxyribonuclease, collagenolytic, debridement, fibrinolytic or proteolytic enzymes, papain, papain-urea, and the like; antihistamines such as chlorcyclizine hydrochloride, diphenylhydramine hydrochloride, tripelennamine hydrochloride, and the like; antiepileptics such as nitrazepam, meprobamate, clonazepam, and the like; coronary vasodilators such as nitroglycerine, dipyridamole, erythritol, tetranitrate, pentaerythritol tetranitrate, propatyinitrate, and the like; dermatological agents such as retinal, retinol, retinoic acid and their derivatives, hydroxyacids, alphaketoacids, and the like; and other drugs such as benzoyl peroxide, podofilox, masoprocol, nicotine, scopolamine, nitroglycerine, fluorouracil, hydrocolloids, hydroquinone, monobenzone, tretinoin and acyclovir. Preferred drugs for use herein include acne-benzoyl peroxide, Vitamin C, and Vitamin E.

Although the one or more active agent(s) incorporated in the microparticles are preferably hydrophilic, the subject matter includes the incorporation of one or more active(s) that are hydrophobic, and the incorporation of a combination of hydrophilic agents and hydrophobic agents.

The microparticles may also comprise one or more matrix binder, or excipient materials. Preferably, the matrix materials are inert or substantially so. Non-limiting examples of matrix materials include binders such as saccharide binders, protein binders, and synthetic polymer binders; fillers such as plant cellulose, dibasic calcium phosphate, vegetable fats and oils, sugar fillers, calcium carbonate, and magnesium stearate; preservatives such as antioxidants, amino acid preservatives, citric acid, sodium citrate, synthetic preservatives such methyl paraben and propyl paraben; sorbents; and other additives.

Utilizing one or more matrix materials in conjunction with one or more active agent(s) enables a formulator to selectively provide a desired concentration of active in the adhesive composition. Furthermore, in certain applications it may be desired to utilize a relatively high concentration or loading of microparticles in the adhesive. Utilizing a matrix material in the microparticles enables selected or relatively low concentrations of active(s) to be attained.

A preferred method of forming microparticles of one or more actives is spray drying. Spray drying is a method of producing a dry powder from a liquid or slurry by rapidly drying with a hot gas. This is the preferred method of drying of many thermally sensitive materials such as foods and pharmaceuticals. A consistent particle size distribution is a reason for spray drying some industrial products such as catalysts. Air is typically the heated drying media. However, if the liquid is a flammable solvent or the product is oxygen-sensitive then nitrogen can be used.

In forming the preferred embodiment microparticles, one or more active agents are placed in a liquid form, if not already in such form. If any matrix materials are used, those are combined with the active(s). Additional amounts of solvent or liquid medium may be added to adjust viscosity as desired. Dispersants and/or surfactants can be added to promote mixing and/or dispersion of the active agent(s) in the solvent or carrier. The liquid is then administered to one or more spray dryers.

All spray dryers use some type of atomizer or spray nozzle to disperse the liquid or slurry into a controlled drop size spray. The most common of these are rotary nozzles and single fluid pressure swirl nozzles. Alternatively, for some applications two-fluid or ultrasonic nozzles are used. Depending on the process requirements, drop sizes from 10 to 500 micrometers can be achieved with the appropriate nozzle selection. The most common drop sizes are in the 100 to 200 micrometer diameter range. The resulting dry powder is often free-flowing.

The hot drying gas can be passed as a co-current or counter-current flow to the atomizer direction. A co-current flow enables the particles to have a lower residence time within the system and the particle separator (typically a cyclone device) operates more efficiently. The counter-current flow method enables a greater residence time of the particles in the chamber and usually is paired with a fluidized bed system.

Microparticles and/or Encapsulated Active Agent(s)

The subject matter also provides additional embodiments in which microparticles of one or more active agents are produced which are then incorporated into an adhesive formulation or adhesive intermediate. The term "microparticles" as used herein refers to particles having an average diameter or span of from about 0.1 microns to about 500 microns, more preferably from about 1 micron to about 200 microns, more preferably from about 5 microns to about 100 microns, and most preferably from about 5 microns to about 50 microns. The preferred embodiment microparticles can be in a variety of different shapes. For example, the microparticles may be spherical, oblong, or in the form of a thin sheet or flake. The term "span" as used herein refers to the maximum dimension of the particle. Preferably, the microparticles are spherical or generally so.

The microparticles can be relatively homogenous and exhibit a uniform structure throughout their interior or substantially so. Alternatively, the microparticles can include one or more layers and/or discrete interior regions differing in structure, composition, and/or physical characteristics. A preferred configuration for microparticles containing an active agent is that such microparticles contain an outer layer of a polymer or other material that dissolves or otherwise degrades upon exposure to saline, other bodily fluids, or conditions of basic pH, such as a pH greater than 7. The preferred material for the outer layer is generally referred to herein as a water sensitive material and is described in greater detail herein. These preferred microparticles may in other embodiments, include a core which is preferably hydrophilic. Upon incorporation of the preferred microparticles containing an active agent in an adhesive or adhesive intermediate and subsequent use of the adhesive in a medical product, a delayed release of one or more active agents occurs upon exposure to saline or body fluids. That is, once the outer layer of dissolvable or degradable material is removed, an interior layer or region of the microparticles containing the active agent(s) is exposed, thereby enabling migration of the one or more active agents from the microparticles. This strategy provides a convenient technique for establishing long lasting delivery of active agents.

Although not wishing to bound to any particular theory, it is believed that the inclusion of a hydrophilic core in the preferred embodiment microparticles tends to promote incorporation of one or more active agents, and particularly those which are highly hydrophilic. The core of such microparticles can comprise one or multiple active agents. The outer layer or shell in microparticles having a core and shell construction can be hydrophilic or hydrophobic.

As noted, in certain embodiments in which the active agent(s) are formed into microparticles, it may be preferred to provide one or more outer layers of a water sensitive polymer that dissolves or is otherwise removed upon exposure to certain agents. Non-limiting examples of such polymers include starch; materials based on amylase; polysaccharides such as cellulose and derivates, chitin, chitosan, dextran, alginate; proteins such as casein, albumin, gelatin; and synthetic polymers such as polyvinyl pyrolidone, polyethylene oxide, polyvinyl alcohol. Combinations of these materials can be used. For certain charged antimicrobials, a charged polymer can be used to assist in the delivery and/or retention of the antimicrobial.

For embodiments in which one or more active agents are incorporated within the interior of microparticles, the release of the active agent can generally be controlled by the following parameters—the diameter or span of the microparticles, the proportion of water sensitive polymer as compared to the amount of the active agent, the nature of the water sensitive polymer and particularly its dissolution rate, and the chemistry of the adhesive and its sensitivity to moisture, water, or other agents.

The various versions of the preferred embodiment microparticles comprising one or more active agents can be prepared in a variety of techniques. A preferred technique is to use a spray drying operation as described herein to form the noted microparticles. One or more outer layers and preferably layer(s) of a water sensitive material can be applied or otherwise deposited upon the outer surface of the microparticles by techniques known in the art.

In a preferred aspect, microparticles of one or more active agents consisting of a core embedded into a water sensitive polymer are produced by a spray drying process. Upon incorporation in an adhesive matrix, solid microparticles will release the one or more active agents over a relatively long period of time.

Incorporation of Microparticles in Adhesive

As previously noted, for embodiments in which the active agent(s) is in the form of coated microparticles exhibiting a delayed release characteristic, the microparticles can be incorporated directly into an adhesive formulation by blending and/or mixing.

The adhesive containing the microparticles of active agent(s) are then incorporated in a product or used as desired. For example, conventional coating and drying operations can be performed to form an adhesive layer on a medical product. Representative non-limiting examples of such medical products include surgical goods such as incise films, and device fixation products; wound care products; and ostomy pouches.

In certain embodiments, the adhesive can be covered with a carrier, preferably a polyurethane film or any alternative material.

Adhesives

The methods of the present subject matter can be used to incorporate one or more active agents into a wide array of adhesives, and preferably a solvent based adhesive or a hot melt adhesive. Non limiting examples of suitable types of adhesives include acrylic adhesives, rubber adhesives, silicone adhesives, polyurethane adhesives, and variants and combinations thereof. Generally, the resulting microparticles of active agent(s) can be incorporated into nearly any non-aqueous based adhesive. Preferably, the adhesive is a solvent based adhesive. More preferably, the adhesive is a solvent based acrylic adhesive.

The present subject matter also includes combining microparticles of one or more active agent(s) with an adhesive component such as an adhesive ingredient and/or an adhesive premix. This strategy provides an alternative approach for subsequent formation of an adhesive comprising actives in the form of delayed release microparticles.

For embodiments in which the one or more active agents are hydrophilic and in a microparticle form, another advantage results when the microparticles are incorporated into a hydrophobic adhesive matrix. Due to their hydrophilic properties, such active agents will easily release from a hydrophobic adhesive matrix.

The preferred embodiment adhesive compositions include the microparticles as described herein in a proportion of from about 0.01% to about 50% or more, by weight, based upon the total weight of the adhesive. Preferably, the microparticles constitute from about 0.1% to about 40% by weight, and most preferably from about 1% to about 30% by weight of the adhesive composition.

Additional Additives

One or more additional additives can be incorporated into the adhesive and active microparticle formulation. Preferably the additional additives include medicinal compounds. Such medicinal compounds include, but are not limited to, antimicrobials, antibiotics, antifungal agents, antiviral agents, antithrombogenic agents, anesthetics, anti-inflammatory agents, analgesics, anticancer agents, vasodilation substances, wound healing agents, angiogenic agents, angiostatic agents, immune boosting agents, growth factors, and other biological agents. Suitable antimicrobial agents include, but are not limited to, biguanide compounds; triclosan; penicillins; tetracyclines; aminoglycosides, such as gentamicin and Tobramycin™; polymyxins; rifampicins; bacitracins; erythromycins; vancomycins; neomycins; chloramphenicols; miconazole; quinolones, such as oxolinic acid, norfloxacin, nalidixic acid, pefloxacin, enoxacin, and ciprofloxacin; sulfonamides; nonoxynol 9; fusidic acid; cephalosporins; and combinations of such compounds and similar compounds. The additional antimicrobial compounds provide for enhanced antimicrobial activity.

The present subject matter is believed to provide a significant advance in the art. For example, use of the preferred embodiment adhesive composition with delayed release microparticles can provide extended release of one or more active agents over relatively long periods of time, such as over a time period of at least 3 days, or at least 5 days, or at least 7 days for example. Furthermore, the preferred embodiment adhesive formulations can be used to administer two or more otherwise incompatible actives in the same formulation. Thus, one population of microparticles containing a first active and another population of microparticles containing a second active which is incompatible with the first active can be provided. In addition, use of the preferred embodiment adhesives as described herein can be formulated to protect an active agent from oxidation and/or degradation during an adhesive coating process. Moreover, the composition can be tailored to trigger release of the one or more active agents upon occurrence of certain conditions such as for example existence of a particular pH, moisture level, and/or presence of certain enzymes.

Many other benefits will no doubt become apparent from future application and development of this technology.

All patents, published applications, and articles noted herein are hereby incorporated by reference in their entirety.

It will be understood that any one or more feature or component of one embodiment described herein can be combined with one or more other features or components of another embodiment. Thus, the present subject matter includes any and all combinations of components or features of the embodiments described herein.

As described hereinabove, the present subject matter solves many problems associated with previous type products, adhesives and practices. However, it will be appreciated that various changes in the details, materials and arrangements of components and operations, which have been herein described and illustrated in order to explain the nature of the subject matter, may be made by those skilled in the art without departing from the principle and scope of the subject matter, as expressed in the appended claims.

What is claimed is:

1. An adhesive composition comprising:
an adhesive;
microparticles dispersed in the adhesive, the microparticles including a matrix material and at least one active agent;
wherein at least one active agent is hydrophilic;
wherein at least one active agent is chlorhexadine gluconate;
wherein the matrix material is a saccharide binder;
wherein the adhesive is selected from the group consisting of acrylic adhesives, rubber adhesives, and combinations thereof; and
wherein the microparticles further include an outer layer of a water sensitive material that dissolves or otherwise degrades upon exposure to at least one of (i) saline, (ii) other bodily fluids, and basic pH.

2. The adhesive of claim 1 wherein the water sensitive material includes an agent selected from the group consisting of starch, materials based on amylase, polysaccharides, proteins, synthetic polymers, and combinations thereof.

3. The adhesive of claim 2 wherein the water sensitive material is starch.

4. The adhesive of claim 2 wherein the water sensitive material is a material based on amylase.

5. The adhesive of claim 2 wherein the water sensitive material is a polysaccharide.

6. The adhesive of claim 5 wherein the polysaccharide is selected from the group consisting of cellulose and its derivatives, chitin, chitosan, dextran, alginate, and combinations thereof.

7. The adhesive of claim 2 wherein the water sensitive material is a protein.

8. The adhesive of claim 7 wherein the protein is selected form the group consisting of casein, albumin, gelatine, and combinations thereof.

9. The adhesive of claim 2 wherein the water sensitive material is a synthetic polymer.

10. The adhesive of claim 9 wherein the synthetic polymer is selected from the group consisting of polyvinyl pyrolidone, polyethylene oxide, polyvinyl alcohol, and combinations thereof.

11. The adhesive composition of claim 1 wherein the microparticles constitute from about 0.01% to about 50% by weight of the total weight of the composition.

12. The adhesive composition of claim 11 wherein the microparticles constitute from about 0.1% to about 40% by weight of the total weight of the composition.

13. The adhesive composition of claim 12 wherein the microparticles constitute from about 1% to about 30% by weight of the total weight of the composition.

\* \* \* \* \*